(12) United States Patent
Huang

(10) Patent No.: US 12,083,252 B1
(45) Date of Patent: Sep. 10, 2024

(54) FRAGRANCE CARRIER HOLDER

(71) Applicant: Kongxie Huang, Fuzhou (CN)

(72) Inventor: Kongxie Huang, Fuzhou (CN)

( * ) Notice: Subject to any disclaimer, the term of this patent is extended or adjusted under 35 U.S.C. 154(b) by 0 days.

(21) Appl. No.: 18/432,452

(22) Filed: Feb. 5, 2024

(30) Foreign Application Priority Data

Jan. 16, 2024 (CN) .......................... 202420106331.2

(51) Int. Cl.
*A61L 9/12* (2006.01)
*A61L 9/05* (2006.01)

(52) U.S. Cl.
CPC .. *A61L 9/12* (2013.01); *A61L 9/05* (2013.01)

(58) Field of Classification Search
CPC ........................................................ A61L 9/12
USPC ........................................... 239/59; 220/483
See application file for complete search history.

(56) References Cited

U.S. PATENT DOCUMENTS

| | | | | |
|---|---|---|---|---|
| 3,848,803 A | * | 11/1974 | Levey ...................... | A61L 9/12 428/905 |
| 3,976,246 A | * | 8/1976 | Hauri ..................... | B65D 83/00 239/57 |
| 4,241,856 A | * | 12/1980 | Otterson ................ | B65D 25/50 215/221 |
| 5,913,313 A | * | 6/1999 | Brunderman .......... | A61B 17/54 132/200 |
| 9,833,533 B2 | * | 12/2017 | Baranowski ............. | A61L 9/14 |

* cited by examiner

*Primary Examiner* — Stephen J Castellano

(57) ABSTRACT

A fragrance carrier holder, including: a rear wall, configured to face a mounting surface; a front wall, opposite to the rear wall; a side wall, connected to the front wall and the rear wall; and a cover body, rotatably disposed on a side of the front wall back away from the rear wall; wherein the side wall defines a first opening and a second opening opposite to the first opening; the rear wall defines a plurality of rear-wall through holes, and the front wall defines a plurality of front-wall through holes; the cover body is configured to cover or expose the plurality of front-wall through holes in response to being rotated.

5 Claims, 2 Drawing Sheets

FRAGRANCE CARRIER HOLDER

CROSS REFERENCE TO RELATED APPLICATIONS

The present application claims foreign priority of Chinese Patent Application No. 202420106331.2, filed on Jan. 16, 2024, in the China National Intellectual Property Administration, the entire contents of which are hereby incorporated by reference in its entirety.

TECHNICAL FIELD

The present disclosure relates to the technical field of scenting devices, and especially relates to a fragrance carrier holder.

BACKGROUND

With the improvement of living standards, people pay more and more attention to the quality of all aspects of life. In family life, the indoor air quality directly affects people's mood. Especially after a busy day of work, the air environment in the bathroom shower directly affects people's physical and mental state of relaxation.

One way to improve the quality of the air environment in the bathroom is to apply a soluble fragrance carrier, commonly known as a "shower tab", in the bathroom. Typically, the shower tab is placed on the floor of the shower stall, and water from the shower head dissolves the tab and releases the scent.

However, due to the lack of control over the water flow in the shower and the fact that the shower tab cannot be moved after being placed, the shower tab is always dissolved within a short period of time, shortening the fragrance experience considerably, and the residue of the shower tab on the floor is not easy to clean up, which affects the aesthetics of the bathroom.

SUMMARY OF THE DISCLOSURE

Based on this, it is necessary to propose a fragrance carrier holder to solve the problem of the fragrance carrier dissolving too quickly and the residue being difficult to clean.

A fragrance carrier holder, including: a rear wall, configured to face a mounting surface;

a front wall, opposite to the rear wall; a side wall, connected to the front wall and the rear wall; and a cover body, rotatably disposed on a side of the front wall back away from the rear wall; wherein the side wall defines a first opening and a second opening opposite to the first opening; the rear wall defines a plurality of rear-wall through holes, and the front wall defines a plurality of front-wall through holes; the cover body is configured to cover or expose the plurality of front-wall through holes in response to being rotated.

In some embodiments, an area of the first opening is greater than an area of the second opening.

In some embodiments, a side of the rear wall facing the front wall is arranged with a plurality of protrusions.

In some embodiments, the fragrance carrier holder further includes a plurality of suction cups arranged on a side of the rear wall back away from the front wall.

In some embodiments, the front wall, the rear wall, the side wall, and the plurality of suction cups are of a one-piece structure and made of a flexible material.

In some embodiments, the cover body is detachably connected to the front wall, the cover body including a lower cover and an upper cover that at least partially cover the front wall; the upper cover protrudes from the lower cover and is arranged with an anti-slip pattern.

In some embodiments, the side wall extends at an angle from the first opening to the second opening.

The fragrance carrier holder provided by the present disclosure includes: a rear wall configured to face a mounting surface, a front wall opposite to the rear wall, and a side wall connected to the front wall and the rear wall; the side wall defines a first opening and a second opening opposite to the first opening; the rear wall defines multiple rear-wall through holes; the fragrance carrier holder further includes a cover body rotatably disposed on a side of the front wall back away from the rear wall; the front wall defines multiple front-wall through holes; the cover body is configured to cover or expose the front-wall through holes when rotated. By utilizing the holder to support the fragrance carrier, and by arranging the cover body to cover or expose the front-wall through holes when rotated, the size of the water flow to the fragrance carrier can be controlled, thereby prolonging the dissolution time of the fragrance carrier and avoiding direct contact of residue with the floor.

BRIEF DESCRIPTION OF THE DRAWINGS

In order to more clearly illustrate the technical solutions in the specific embodiments of the present disclosure or the related art, the following will briefly introduce the accompanying drawings that need to be used in the specific embodiments or related art. It is obvious that the attached drawings in the following description are some of the embodiments of the present disclosure. For those skilled in the art, other accompanying drawings may be obtained from these drawings without creative effort.

DETAILED DESCRIPTION

The following will be a clear and complete description of the technical solution of the present disclosure in conjunction with the accompanying drawings. Obviously, the described embodiments are part of the embodiments of the present disclosure, not all of them. Based on the embodiments in the present disclosure, all other embodiments obtained by those skilled in the art without making creative labor belong to the scope of the present disclosure.

In the description of the present disclosure, it should be noted that if terms "center", "upper", "lower", "left", "right", "vertical", "horizontal", "inside", "outside", etc. are used, the orientation or position relationship indicated therein is based on the orientation or position relationship shown in the accompanying drawings and is only for the purpose of facilitating and simplifying the description of the present disclosure, not to indicate or imply that the device or component referred to must have a specific orientation, be constructed and operated in a specific orientation, and therefore cannot be construed as a limitation of the present disclosure. In addition, the terms "first", "second", and "third" are used for descriptive purposes only, and are not to be construed as indicating or implying relative importance.

Figure 1:
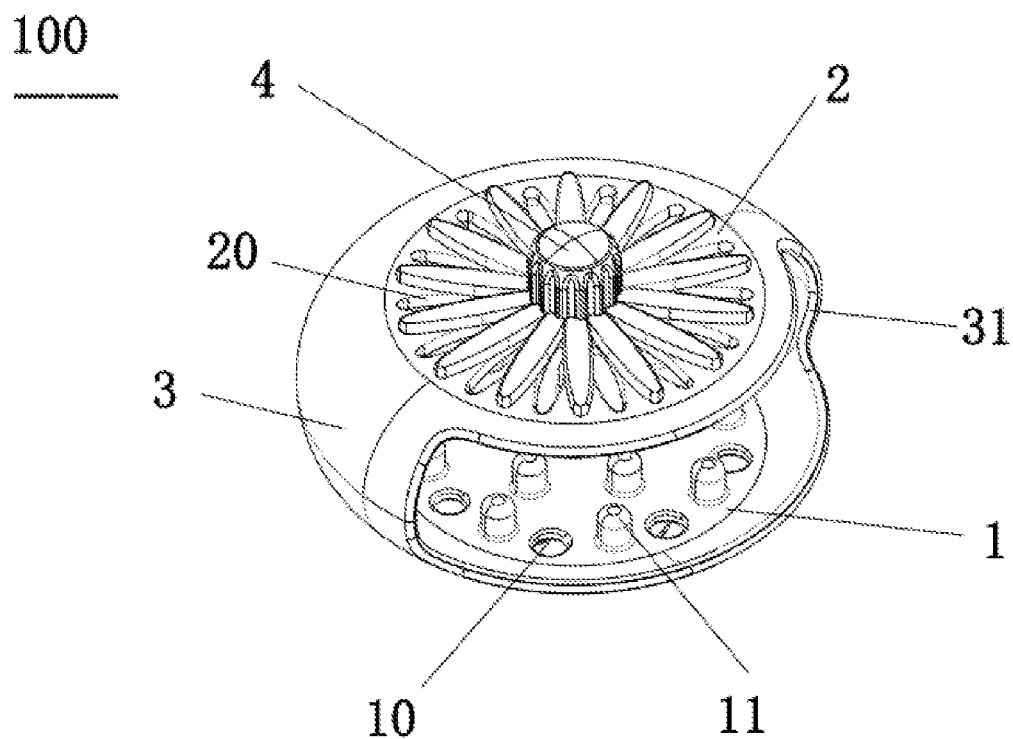
FIG. 1 is an assembly schematic view of a fragrance carrier holder according to some embodiments of the present disclosure.
Figure 2:
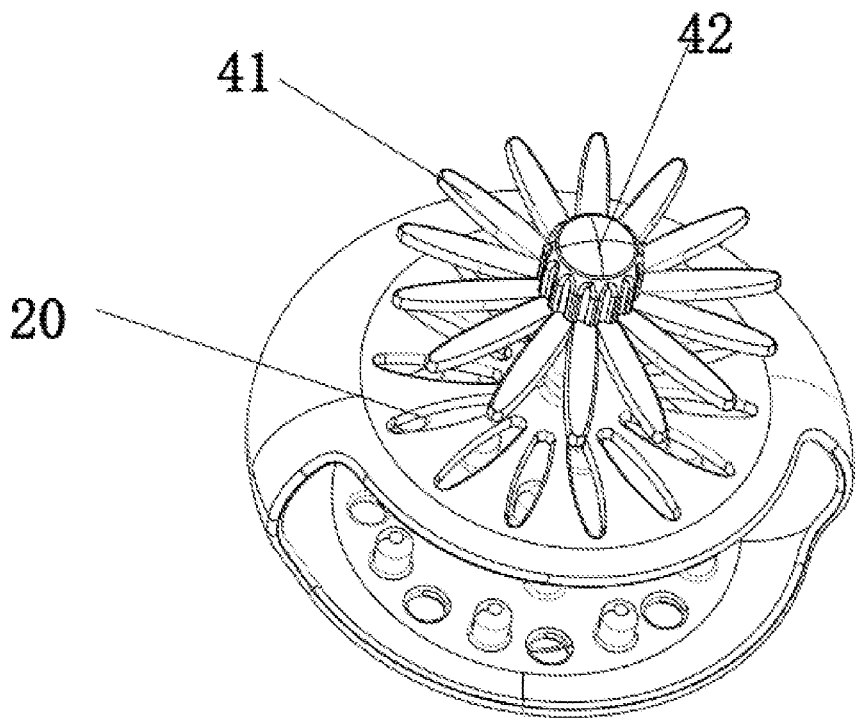
FIG. 2 is a disassembled schematic view of a fragrance carrier holder according to some embodiments of the present disclosure.
Figure 3:
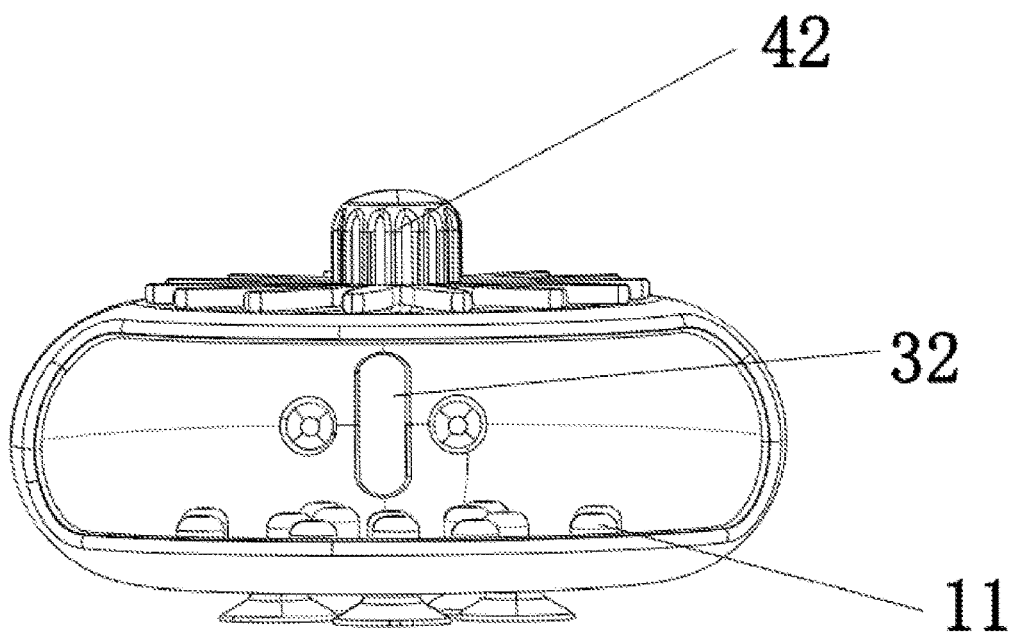
FIG. 3 is a schematic view the fragrance carrier holder shown in FIG. 1 at another viewing angle.
Figure 4:
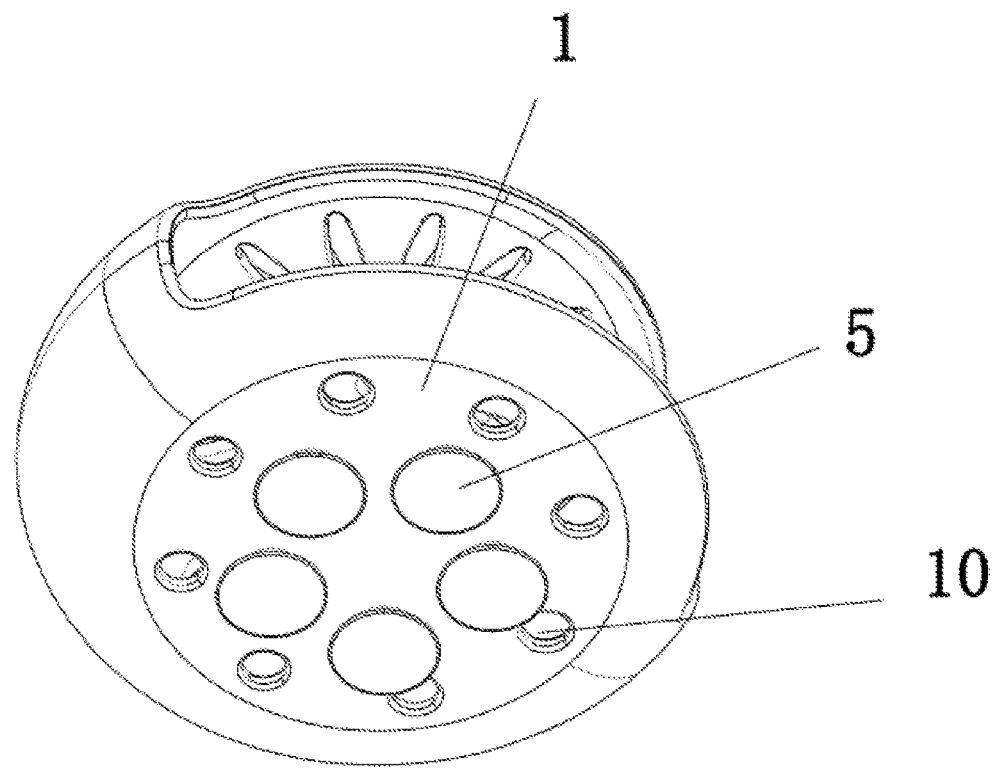
FIG. 4 is a schematic view the fragrance carrier holder shown in FIG. 1 at further another viewing angle.

As shown in FIGS. 1-FIG. 4, the present disclosure provides a fragrance carrier holder 100, including: a rear wall 1 configured to face a mounting surface, a front wall 2 opposite to the rear wall 1, and a side wall 3 connected to the front wall 2 and the rear wall 1. The side wall 3 defines a first opening 31 and a second opening 32 opposite to the first opening 31; the rear wall 1 defines multiple rear-wall through holes 10, and the front wall 2 defines multiple front-wall through holes 20. In this way, when the fragrance carrier holder 100 is mounted in a bathroom, regardless that the fragrance carrier holder 100 is mounted with the front wall facing upwards on the bathroom floor or with the front wall facing outwards on the bathroom wall, the water can flow from the first opening 31 into the fragrance carrier holder 100 and then out of the second opening 32, also from the front-wall through holes 20 and then out of the rear-wall through holes 10.

The fragrance carrier holder 100 further includes a cover body 4 rotatably disposed on a side of the front wall 2 back away from the rear wall 1, the cover body 4 being configured to cover or expose the front-wall through holes 20 when rotated. Specifically, the cover body 4 is detachably connected to the front wall 2, the cover body 4 including a lower cover 41 and an upper cover 42 that at least partially cover the front wall 2; the upper cover 42 protrudes from the lower cover 41 and is arranged with an anti-slip pattern. It is to be understood that the shape of the front-wall through holes 20 corresponds to the lower cover 41. When the upper cover 42 is rotated, the lower cover 41 is rotated and can either completely cover the front-wall through holes 20 or partially cover the front-wall through holes 20 or completely expose the front-wall through holes 20. By rotating the cover body 4, the size of the front-wall through holes 20 exposed can be adjusted, such that the size of water flow from the front-wall through holes 20 into the fragrance carrier holder 100 can be controlled.

In some embodiments, the side wall 3 extends at an angle from the first opening 31 to the second opening 32, with the area of the first opening 31 being greater than the area of the second opening 32. In the embodiments, the front wall 2 and the rear wall 1 are each circular and the side wall 3 is curved. In other embodiments, the front wall 2 and the rear wall 1 may each be diamond shaped and the side wall 3 is flat and inclined. It is to be understood that the area of the first opening 31 is not less than a maximum cross-sectional area of a fragrance carrier that can be placed into the fragrance carrier holder 100; the number of the second openings 32 may be one or more, and the sum of the areas of the multiple second openings 32 is still less than the area of the first opening 31.

In some embodiments, a side of the rear wall 1 facing the front wall 2 is arranged with multiple protrusions 11, the protrusions 11 may support the fragrance carrier placed in the fragrance carrier holder 100 to maximize its contact area with the water flow for full dissolution.

In the embodiments, the fragrance carrier holder 100 further includes multiple suction cups 5 arranged on a side of the rear wall 1 back away from the front wall 2, allowing the fragrance carrier holder 100 to be easily mounted to the bathroom floor or wall. The front wall 2, the rear wall 1, the side wall 3, and the suction cups 5 may be of a one-piece structure and made of a flexible material, such as silicone. Further, the cover body 4 may be of the same flexible material. In this way, the fragrance carrier holder 100 is simple and easy to use and easy to clean. It can be understood that the fragrance carrier holder 100 may further be applied in a car, bedroom, and other environments.

The fragrance carrier holder provided by the present disclosure includes: a rear wall configured to face a mounting surface, a front wall opposite to the rear wall, and a side wall connected to the front wall and the rear wall; the side wall defines a first opening and a second opening opposite to the first opening; the rear wall defines multiple rear-wall through holes; the fragrance carrier holder further includes a cover body rotatably disposed on a side of the front wall back away from the rear wall; the front wall defines multiple front-wall through holes; the cover body is configured to cover or expose the front-wall through holes when rotated. By utilizing the holder to support the fragrance carrier, and by arranging the cover body to cover or expose the front-wall through holes when rotated, the size of the water flow to the fragrance carrier can be controlled, thereby prolonging the dissolution time of the fragrance carrier and avoiding direct contact of residue with the floor.

The above embodiments are only intended to illustrate the technical solution of the present disclosure, not to limit the same; despite the detailed description of the present disclosure with reference to the preceding embodiments, those skilled in the art should understand that it is still possible to modify the technical solutions recorded in the preceding embodiments, or to replace some or all of them with equivalent technical features; and these modifications or replacements do not make the essence of the corresponding technical solutions out of the scope of the technical solutions of the embodiments of the present disclosure.

What is claimed is:

1. A fragrance carrier holder, comprising:
a rear wall, configured to face a mounting surface;
a front wall, opposite to the rear wall;
a side wall, connected to the front wall and the rear wall; and
a cover body, rotatably disposed on a side of the front wall back away from the rear wall;
wherein the side wall defines a first opening and a second opening opposite to the first opening; the rear wall defines a plurality of rear-wall through holes, and the front wall defines a plurality of front-wall through holes; the cover body is configured to cover or expose the plurality of front-wall through holes in response to being rotated;
the fragrance carrier holder further comprises a plurality of suction cups arranged on a side of the rear wall back away from the front wall;
wherein the front wall, the rear wall, the side wall, and the plurality of suction cups are of a one-piece structure and made of a flexible material.

2. The fragrance carrier holder according to claim 1, wherein an area of the first opening is greater than an area of the second opening.

3. The fragrance carrier holder according to claim 1, wherein a side of the rear wall facing the front wall is arranged with a plurality of protrusions.

4. The fragrance carrier holder according to claim 1, wherein the cover body is detachably connected to the front wall, the cover body comprising a lower cover and an upper cover that at least partially cover the front wall; the upper cover protrudes from the lower cover and is arranged with an anti-slip pattern.

5. The fragrance carrier holder according to claim 1, wherein the side wall extends at an angle from the first opening to the second opening.

* * * * *